United States Patent [19]

Desai et al.

[11] Patent Number: 5,383,917
[45] Date of Patent: Jan. 24, 1995

[54] DEVICE AND METHOD FOR MULTI-PHASE RADIO-FREQUENCY ABLATION

[75] Inventors: Jawahar M. Desai, 4141 Cowell Blvd. No. 38, Davis, Calif. 95616; Htay L. Nyo, San Jose, Calif.

[73] Assignee: Jawahar M. Desai, Roseville, Calif.

[21] Appl. No.: 726,035

[22] Filed: Jul. 5, 1991

[51] Int. Cl.$^6$ ............................................. A61N 5/00
[52] U.S. Cl. ................................. 607/702; 607/101; 607/122; 607/154; 606/31; 606/42
[58] Field of Search .............. 128/784, 786, 799, 642, 128/804; 606/27, 31, 41, 42; 607/116, 119, 122, 148, 154, 96, 98, 99, 101, 102

[56] References Cited

U.S. PATENT DOCUMENTS

| | | |
|---|---|---|
| 4,365,639 | 12/1982 | Goldreyer . |
| 4,565,200 | 1/1986 | Cosman ............................ 128/642 |
| 4,660,571 | 4/1987 | Hess et al. ....................... 128/786 |
| 4,940,064 | 7/1990 | Desai . |
| 5,122,137 | 6/1992 | Lennox ............................. 606/42 |
| 5,156,151 | 10/1992 | Imran ............................... 128/642 |

OTHER PUBLICATIONS

Desai et al., "Orthogonal electro catheter array for mapping of endocardiac local site", *Pacing and clinical electrophysiology* and, vol. 14, pp. 557–574, (Apr., 1992).
Haines and Watson, "Tissue heating during radio-frequency catheter abalation abalation", *Pace* and, vol. 12, 1989, pp. 962–976.
Desai et al., "Endocardial Isochronal Patters near the Ventricular Tachycardia Site of Origin with Orthogonal Electrode Catheter Array", *JACC* vol. 13, No. 2, Feb. 1989, p. 167A (Abstract Only).
Desai et al., "Two Phase Radiofrequency Ablation of Isolated Ventricular Endocardium", *PACE* vol. 12, Apr. 1989, Part I, p. 657 (Abstract Only).
Desai et al., "Two Phase Radiofrequency Ablation", Journal of Pacing and Clinical Electrophysiology, vol. 14, Jul. 1991, Article No. 2987B.
Morady et al., "Catheter Ablation of Ventricular Tachycardia with Intracardiac Shocks: results in 33 patients", *Circulation*, vol. 75, No. 5, May 1987, pp. 1037–1049.
Altman, "New Therapy Combats 2 Types of Racing Heart", The New York Times National, Jun. 6, 1991, p. A16.

Primary Examiner—William E. Kamm
Assistant Examiner—Kennedy J. Schaetzle
Attorney, Agent, or Firm—Majestic, Parsons, Siebert & Hsue

[57] ABSTRACT

Multi-phase RF ablation employing a two-dimensional or three-dimensional electrode array produces a multitude of currents paths on the surface of the ablation zone. This results in a uniform lesion with a size defined by the span of the electrode array. An orthogonal electrode catheter array suitable for cardiac ablation is used in conjunction with a two-phase RF power source to produce uniform square-shaped lesions of size 1.2 cm$^2$. Lesions of larger size are created by successive adjacent placement of the square-shaped lesions. A temperature sensor at the electrode tip allows monitoring of ablation temperature and regulation of thereof to minimize the electrode tips from being fouled by coagulum.

22 Claims, 9 Drawing Sheets

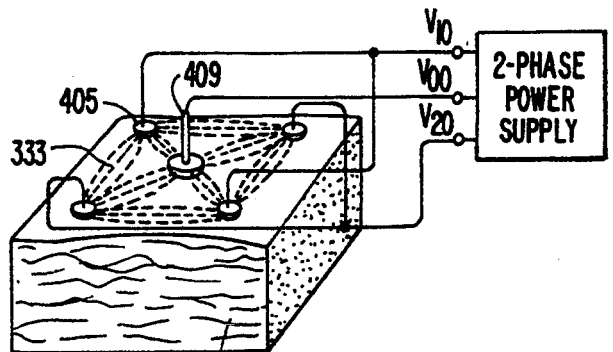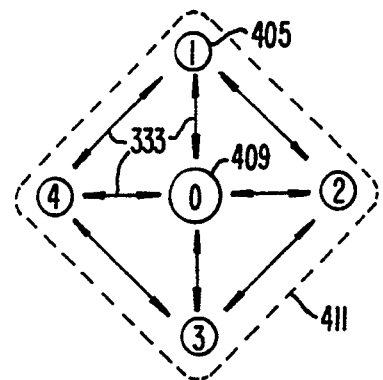
*FIG. 8a.*
*FIG. 8b.*
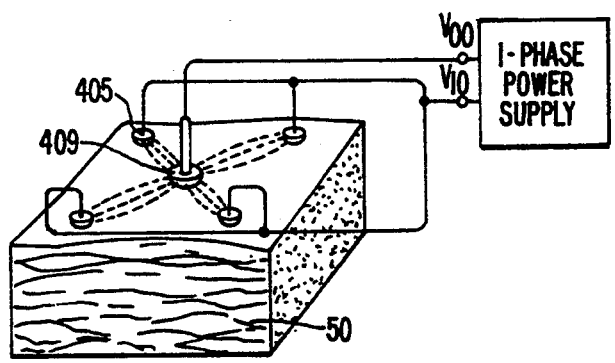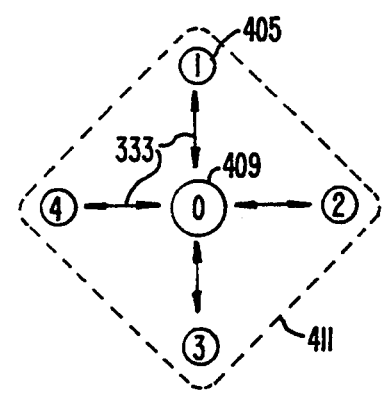
*FIG. 9a.*
*FIG. 9b.*
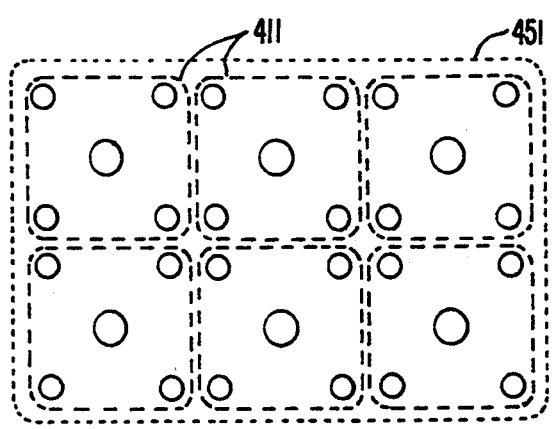
*FIG. 11.*
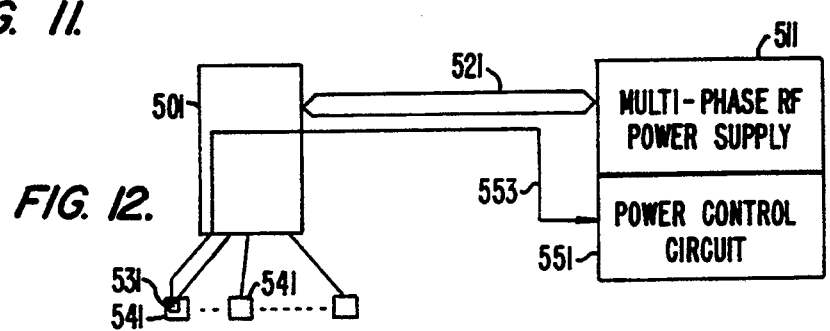
*FIG. 12.*

DEVICE AND METHOD FOR MULTI-PHASE RADIO-FREQUENCY ABLATION

BACKGROUND OF THE INVENTION

This invention relates to medical devices and, in particular, a multi-electrode catheter and techniques therefor of employing multi-phase radio-frequency power source for ablation of endocardiac tissues.

Cardiac dysrhythmias are commonly known as irregular heart beats or racing heart. Two such heart rhythm irregularities are the Wolff-Parkinson-White syndrome and atrioventricular (AV) nodal reentrant tachycardia. These conditions are caused by an extraneous strand of muscle fiber in the heart that provides an abnormal short-circuit pathway for electric impulses normally existing in the heart. For example, in one type of the Wolff-Parkinson-White syndrome the accessory pathway causes the electric impulses that normally travel from the upper to the lower chamber of the heart to be fed back to the upper chamber. Another common type of cardiac dysrhythmias is ventricular tachycardia (VT), which is a complication of a heart attack or reduction of blood supply to an area of heart muscle, and is a life threatening arrhythmia.

In the treatment of cardiac dysrhythmias, non-surgical procedures such as management with drugs are favored. However, some dysrhythmias of the heart are not treatable with drugs. These patients are then treated with either surgical resection of VT site of origin or by Automatic implantable cardiovertor defibrillator (AICD). Both procedures have increased morbidity and mortality and are extremely expensive. Even AICD needs major surgical intervention. In addition, some patients of advanced age or illness cannot tolerate invasive surgery to excise tachycardia focus which causes dysrhythmias.

Techniques have been developed to locate regions of tachycardia and to disable their short-circuit function. Electrical energy shocks are applied to ablate the cardiac tissues in those regions so as to produce scars and interrupt conduction.

The regions to be ablated are usually determined by endocardiac mapping. It is a technique that typically involves percutaneously introducing an electrode catheter into the patient. The electrode catheter is passed through a blood vessel, like femoral vein or aorta and thence into an endocardiac site such as the atrium or ventricle of the heart. A tachycardia is induced and a continuous, simultaneous recording made with a multi-channel recorder while the electrode catheter is moved to different endocardiac positions. When a tachycardial focus is located as indicated in an electrocardiogram recording, it is marked by means of a fluoroscope image.

Upon locating of the tachycardial focus, ablation of cardiac arrhythmias is typically performed by means of a standard electrode catheter. The electrical energy shocks is used to create a lesion in the endocardiac tissues adjacent (i.e. underneath) the standard electrode catheter. By creating one or more lesions, the tachycardial focus may be turned into a region of necrotic tissue, thereby disabling any malfunctions.

Conventional catheter ablation techniques have typically employed a catheter with a single electrode at its tip as one electrical pole. The other electrical pole is formed by a backplate in contact with a patient's external body part. These techniques have been used successfully for interruption or modification of conduction across the atrioventricular (AV) junction in AV nodal reentrant tachycardia; for interruption of accessory pathway in patients with reentrant tachycardia due to Wolff-Parkinson-White Syndrome; and for ablation in some patients with ventricular tachycardia.

In one technique, high voltage direct current (DC) in the range of 100–300 joules is applied across the electrode and the backplate to effect ablation. Direct current energy source using the standard electrode catheter can produce a lesion size larger than the footprint of the electrode. However, the lesion dimensions are variable at the same energy output and they do not have clear demarcation from the surrounding tissues. Additionally, high voltage techniques have other undesirable side-effects such as barotrauma and the lesions formed could become proarrhythmic.

Another technique is to apply a radio-frequency (RF) source to a standard electrode catheter. The RF source is typically in the 600 kHz region and produces a sinusoidal voltage between two wires. When this is delivered between the distal tip of a standard electrode catheter and a backplate, it produces a localized RF heating effect. It causes a well defined, discrete lesion slightly larger than the tip electrode. This simple RF ablation technique creates lesion size sufficient for interruption of AV junction or accessory pathway.

RF ablation is preferable to DC ablation because it does not need anesthesia and produces more circumscribed and discrete lesions and avoids injury caused by high voltages as in DC shock. Generally, catheter ablations of AV junction using standard electrode catheter with DC or RF energy for treating drug resistant supraventricular tachycardia have high success rate with very low incidence of complications.

However, in ventricular tachycardia (VT), endocardiac mapping with a standard electrode catheter can locate the exit site of ventricular tachycardia to within 4–8 $cm^2$ of the earliest site recorded by the catheter. A standard electrode catheter typically has a maximum electrode tip area of about 0.3 $mm^2$. Therefore, the lesion created by the simple RF technique delivered through a standard electrode catheter may not be large enough to ablate the ventricular tachycardia. Attempts to increase the size of lesion by regulation of power and duration by increasing the size of electrode or by regulating the temperature of tip electrode have met with partial success.

In order to increase the size of the lesion, an orthogonal electrode catheter array (OECA) with four peripheral electrodes and one central electrode has been proposed. Such an OECA has been disclosed by Dr. Jawahar Desai in U.S. Pat. No. 4,940,064, issued Jul. 10, 1990, for use in both mapping and ablation of endocardiac sites.

The four peripheral electrodes are actuable from a retracted or collapsed mode. When fanned out, the four peripheral electrodes and the central electrode form an electrode array that typically covers an area of about 0.8 $cm^2$. When used with a conventional RF power source in conjunction with a backplate, the five connecting electrodes will typically produce five lesion spots distributed over the area spanned by the electrode array. However, this arrangement has been found to be unsatisfactory as there are substantial areas between the electrodes that remain unablated. Increasing the power only results in charring of the tissues and early fouling of the electrodes by coagulum formation.

Thus, it is desirable, especially for treating ventricular tachycardia, to have catheter ablations that produce substantially larger, deeper and more uniform lesions than those produced by conventional RF schemes described above.

SUMMARY OF THE INVENTION

Accordingly, it is a general object of the present invention to improve catheter ablations.

It is an object of the present invention to improve cardiac catheter ablations.

It is another object of the present invention to increase the size, depth and uniformity of lesions created by RF catheter ablations.

It is yet another object of the present invention to improve the efficiency of RF catheter ablations.

It is yet another object of the present invention to treat ventricular tachycardia by improved RF catheter ablations.

These and additional objects are accomplished by application of a multi-phase RF power source to a two- or three-dimensional array of electrodes that is deployable from a catheter.

In one embodiment, each electrode is supplied with an RF source having a different phase. In this way, potential differences are created between each pair of electrodes in the array, thereby allowing current to flow between each pair of electrodes in the array to form a more uniform heating pattern therein.

In another embodiment, a simplified power connection configuration provides a phase difference between at least adjacent pairs of electrodes. In this way, potential differences are created between at least adjacent pairs of electrodes in the array, thereby allowing current to flow between each adjacent pair in the array to form a more uniform heating pattern therein.

One important aspect of the present multi-phase RF scheme is that a conventional external contact backplate is not employed to connect to the ground terminal of the power supply to complete the circuit. Instead, one or more electrodes among the array are connected to the ground terminal of the multi-phase RF power supply. In this way, unlike the conventional schemes, the various RF currents do not flow perpendicular into the tissue between the electrodes and a backplate, but instead, flow parallel to the surface of the tissue between different pairs of electrodes. This arrangement allows various permutations of current paths to form on the tissue's surface, thereby adequately filling the ablation zone spanned by the array.

According to a preferred embodiment of the invention, a two-phase RF power source is used in conjunction with an orthogonal electrode catheter array to create a square-shape lesion of size approximately 1.2 cm$^2$. Lesions of larger size can be formed by successive adjacent placements of the electrode array. The orthogonal electrode catheter array comprises a central electrode and four peripheral electrodes. The central electrode is connected to a ground voltage of the power supply. The four peripheral electrodes form two diagonal pairs which are respectively connected to two individually phased voltages of the power supply. By this arrangement RF current is made to flow between all adjacent pairs of electrodes to substantially fill the ablation zone spanned by the array.

According to another aspect of the invention, a temperature sensor is incorporated in at least one of the electrodes so as to monitor and maintain temperature of ablations at a predetermined level.

Additional objects, features and advantages of the present invention will be understood from the following description of the preferred embodiments, which description should be taken in conjunction with the accompanying drawings.

BRIEF DESCRIPTION OF THE DRAWINGS

FIG. 1b illustrates in more detail the ablation region shown in FIG. 1a;

FIG. 1c illustrates schematically the electrode configuration of a multi-electrode catheter with the conventional RF power supply arrangement of FIG. 1a;

FIG. 3b is a schematic block diagram of the phase shifting circuit in FIG. 3a;

FIG. 5b illustrates the current distribution in a subset of adjacent electrodes of the multi-electrode array shown in FIG. 5a;

FIG. 8a illustrates the five-electrode OECA being used as a two-phase ablation apparatus according to a preferred embodiment;

FIG. 8b illustrates the current distributions resulted from the two-phase configuration of FIG. 8a;

FIG. 9a illustrates the five-electrode OECA being connected in a single-phase configuration for the purpose of comparison with the two-phase configuration of FIG. 8a;

FIG. 9b illustrates the current distributions resulted from the single-phase configuration of FIG. 9a;

FIG. 11 illustrates the formation of a still larger lesion by successive adjacent ablations; and FIG. 12 shows a multi-phase RF ablation system having electrode tip temperature control.

DETAILED DESCRIPTION OF THE PREFERRED EMBODIMENTS

Figure 1A:
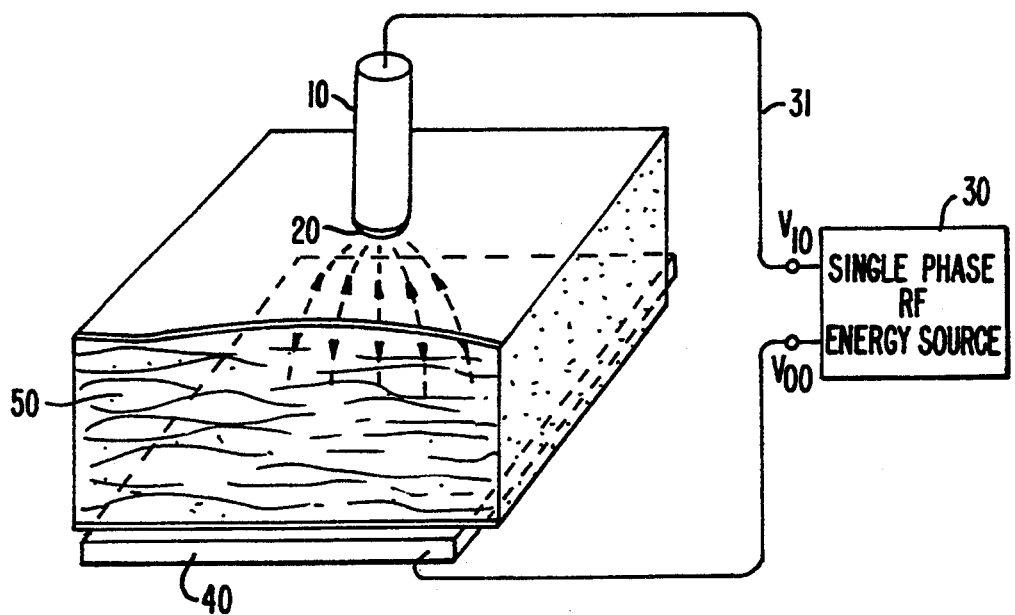
FIG. 1a illustrates the conventional technique of single-phase radio-frequency ablation employing a standard electrode catheter.

FIG. 1a illustrates the conventional technique of single-phase radio-frequency (SPRF) ablation employing a standard electrode catheter 10. An electrode 20 is located at the tip of the catheter and is electrically connected to a single-phase RF energy source or power supply 30. The other end of the power supply 30 is connected to a backplate 40. The electrode 20 is typically hemispheric in shape with a diameter of not more than 0.3 mm so as to allow easy insertion into a patient's body. During operations, the electrode 20 is placed adjacent a region to be ablated such as biological tissues 50 inside a heart (endomyocardium). A closed circuit is formed with the backplate 40 in contact with an external body part near the heart of the patient. RF current spreads perpendicularly from the electrode catheter 20 to the backplate 40 creating a lesion on the endomyocardium 50.

Figure 1B:
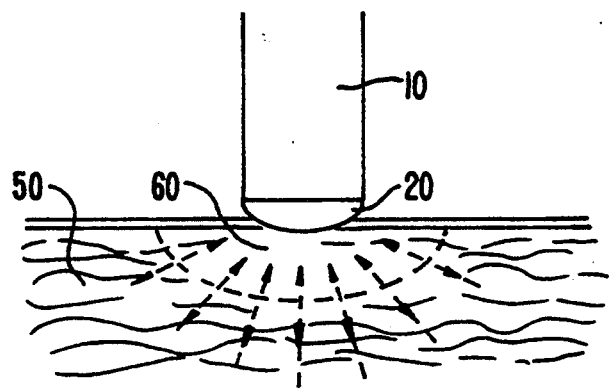

FIG. 1b illustrates in more detail the ablation region shown in FIG. 1a. Since the RF current density is highest at the electrode catheter 20 and decreases rapidly as it flows toward the backplate, the current density will be high enough to cause a lesion 60 in a relatively small region surrounding the electrode catheter.

As discussed earlier, this lesion is probably too small for application in ventricular tachycardia (VT). One possibility of increasing the lesion size is to use an array of electrodes disclosed in U.S. Pat. No. 4,940,064.

Figure 1C:
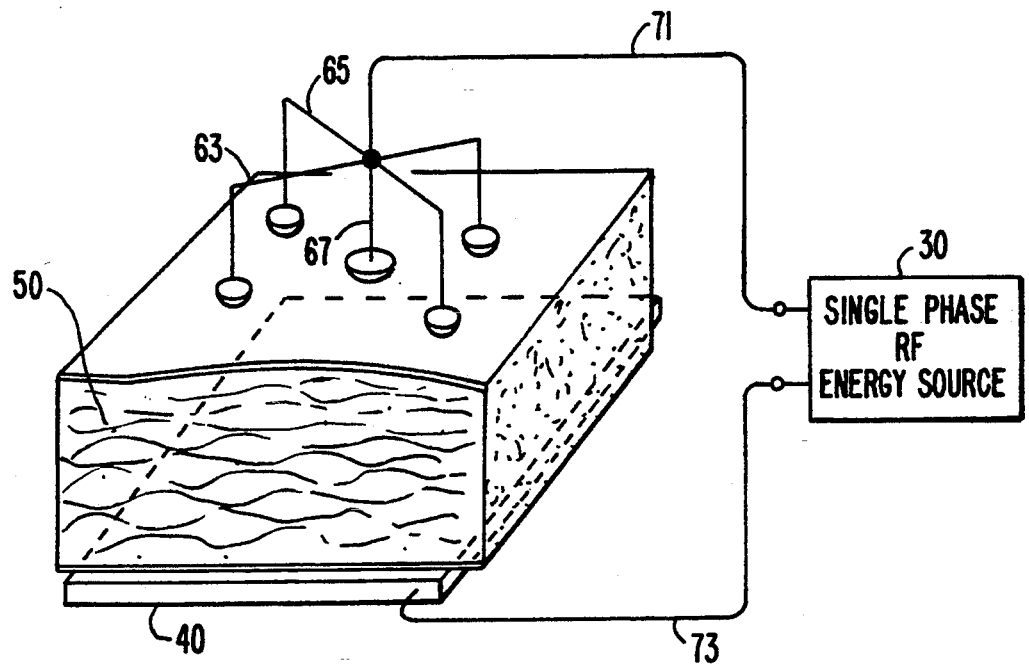

FIG. 1c illustrates schematically the electrode configuration of such a multi-electrode catheter with the conventional RF power supply arrangement of FIG. 1a. It comprises two crossed pairs of electrodes 63, 65 with a fifth, central electrode 67. The multiple electrodes, which are spread evenly over the endomyocardium 50, are all connected to one terminal 71 of the power supply 30, and a backplate 40 is connected to the other terminal 73. RF currents flowing perpendicular to the surface of the endomyocardium 50 will be more spread out.

Figure 1D:
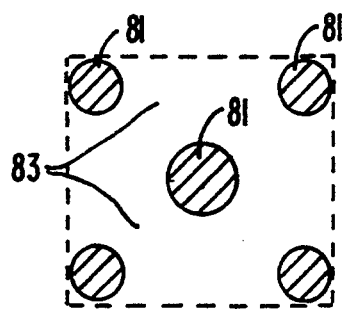
FIG. 1d illustrates the lesions formed by the multi-electrode array of FIG. 1c with conventional perpendicular ablation currents.

FIG. 1d illustrates the lesions formed by such an electrode array with perpendicular ablation currents. The ablation produces discrete lesions 81, each localized about one of the electrodes. Substantial areas 83 in between the electrodes remain unablated.

MULTI-PHASE RF ABLATION

Figure 2A:
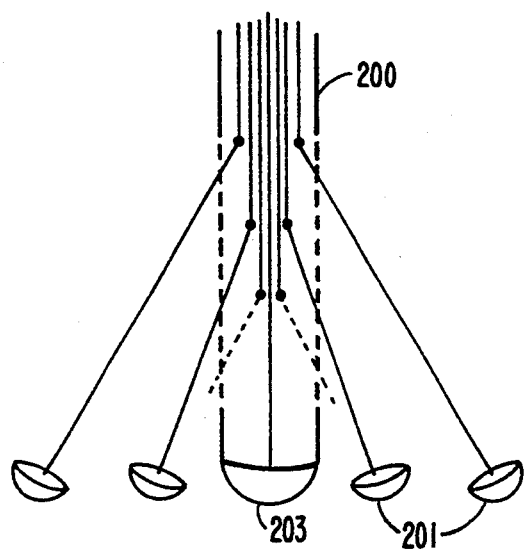
FIG. 2a illustrates schematically a multi-electrode catheter suitable for multi-phase RF ablation.

FIG. 2a illustrates schematically one embodiment of a multi-electrode catheter 200 suitable for multi-phase ablation. The catheter 200 comprises a plurality of electrodes 201 and a centrally located electrode 203. The electrodes are capable of being collapsed onto the catheter body when the catheter is being introduced into a patient's body. During ablation operation they are fanned out into a two-dimensional or three-dimensional array as shown.

Figure 2B:
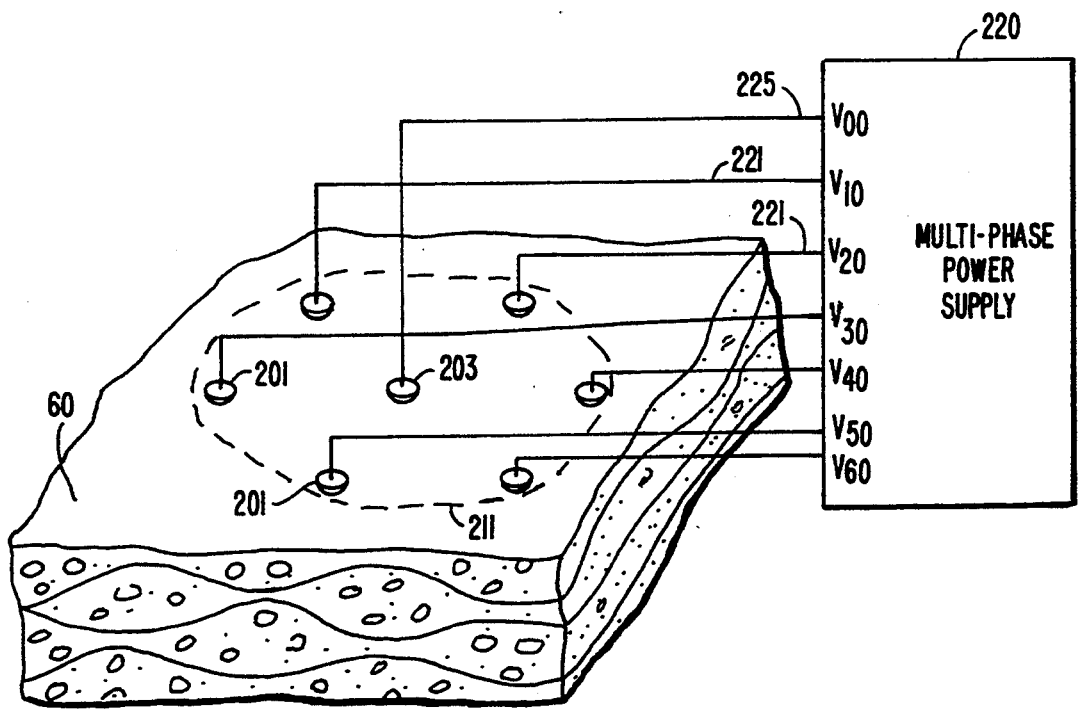
FIG. 2b illustrates schematically the electrical connections of the multi-electrode catheter in FIG. 2a with a multi-phase power supply, according to the present invention.

FIG. 2b illustrates schematically the electrical connections of the multi-electrode catheter in FIG. 2a with a multi-phase power supply. Without loss of generality, a two-dimensional array of seven electrodes 201 are shown. During operations, the array of electrodes is placed adjacent a piece of biological tissue 60, such as a region of endomyocardium to effect ablation thereof. The electrodes 201 are preferably distributed evenly to form an ablation zone 211. Each electrode 201 is connected to a voltage branch $V_{10}$–$V_{60}$ of a multi-phase radio-frequency energy source or power supply 220 by means of an interconnecting wire 221. The centrally located electrode 203 is connected to a ground voltage $V_{00}$ of the power supply 220 via an interconnecting wire 225. The multi-phase RF power supply 220 preferably operates at an RF frequency of about 600 kHz.

Figure 3A:
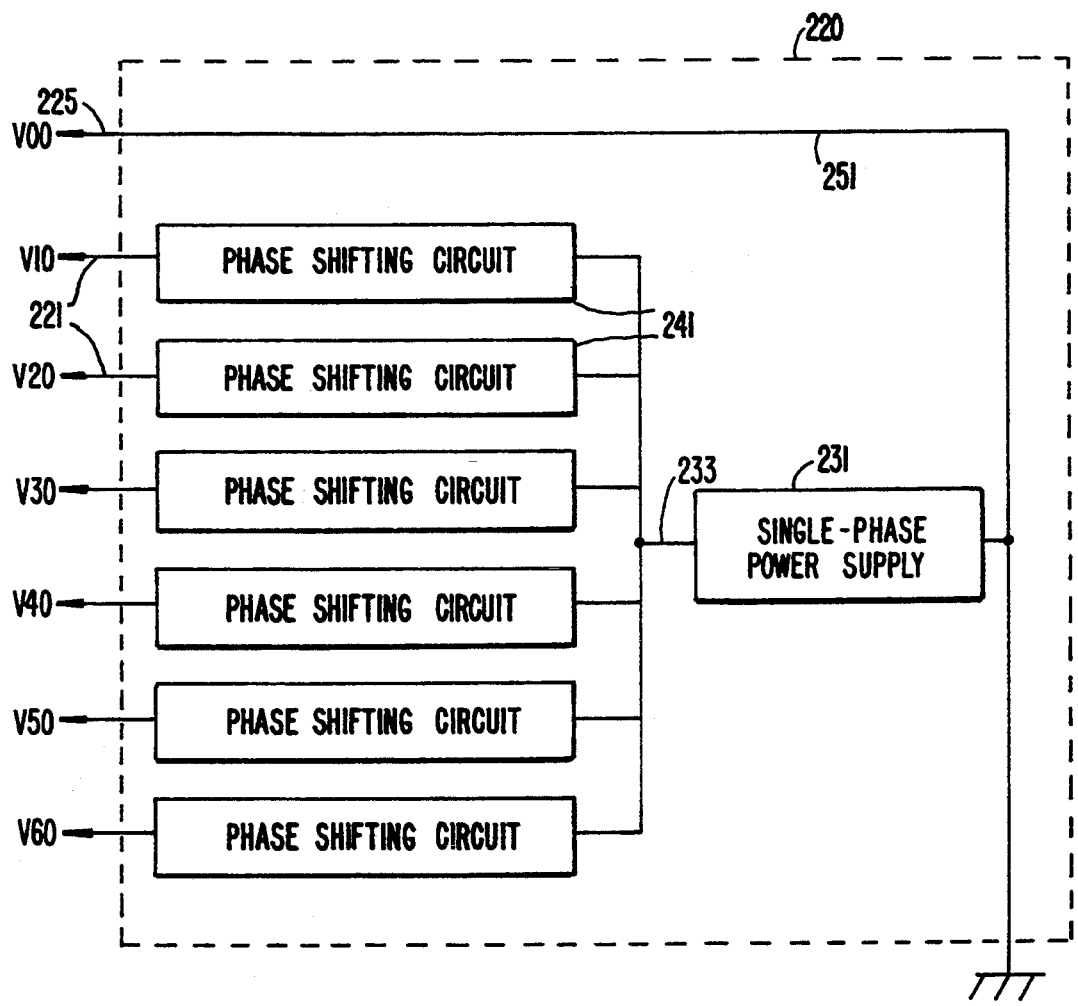
FIG. 3a shows one embodiment of the multi-phase radio-frequency power supply in FIG. 2b.

FIG. 3a shows one embodiment of the multi-phase radio-frequency power supply in FIG. 2b. It comprises a main single-phase power supply 231, the output 233 of which is sent in parallel to a plurality of phase shifting circuits 241. The output voltages $V_{10}$–$V_{60}$ from these phase shifting circuits 241 have substantially the same amplitudes, but their phases are shifted relative to each other. Referring also to FIG. 2b, each individual phased voltage such as $V_{10}$ is supplied via a line 221 to an electrode 201 connected thereto. The central electrode is connected via the interconnecting wire 225 to the ground voltage $V_{00}$ at a terminal 251 of the power supply 220.

Figure 3B:
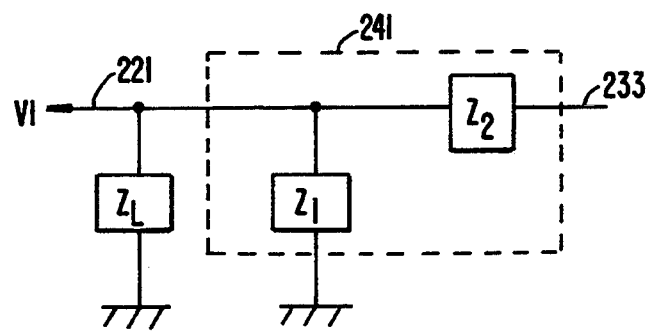

FIG. 3b is a schematic block diagram of the phase shifting circuit 241 in FIG. 3a. It comprises two reactive components $Z_1$, $Z_2$. They can be an RC or RL pair. If $Z_L$ is the load impedance of the electrode, then the phase shift is given by the angle of:

$$Z_1Z_L/[Z_1Z_L+Z_2(Z_1+Z_L)].$$

Figure 4:
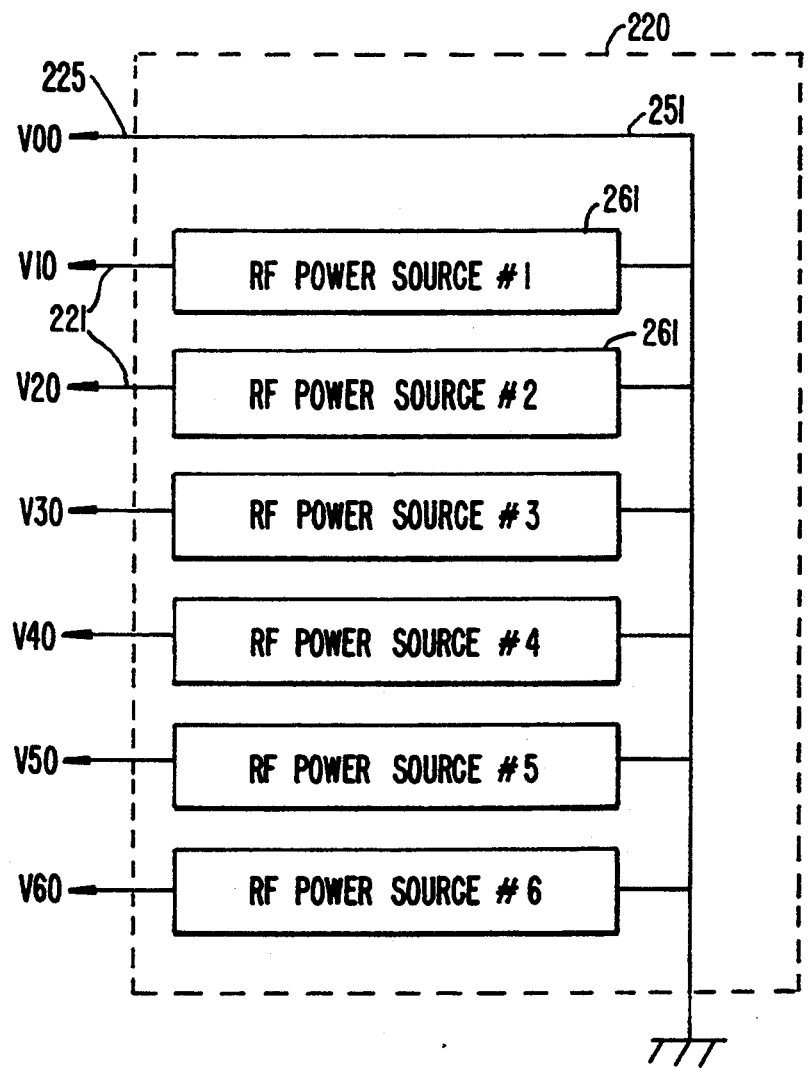
FIG. 4 shows another embodiment of the multi-phase RF power supply in FIG. 2b.

FIG. 4 shows another embodiment of the multi-phase radio-frequency power supply 220 in FIG. 2b. It comprises a plurality of individual RF power source 261. Each individual RF power source 261 is capable of delivering a voltage such as one of $V_{10}$–$V_{60}$ with independent amplitude and phase, one for each electrode 201 connected thereto. The central electrode 203 is connected to a ground voltage $V_{00}$ at the terminal 251.

One important aspect of the present multi-phase RF scheme is that an external contact backplate is not required to connect to the ground terminal of the power supply to complete the circuit. Instead, one or more electrodes among the array are connected to the ground terminal of the multi-phase RF power supply. In this way, unlike the conventional scheme shown in FIGS. 1a and 1b, the various RF currents do not flow perpendicular into the tissue between the electrodes and a backplate, but instead, flow parallel to the surface of the tissue between different pairs of electrodes. This arrangement allows various permutations of current paths to form on the tissue's surface, thereby adequately filling the ablation zone spanned by the array.

Figure 5A:
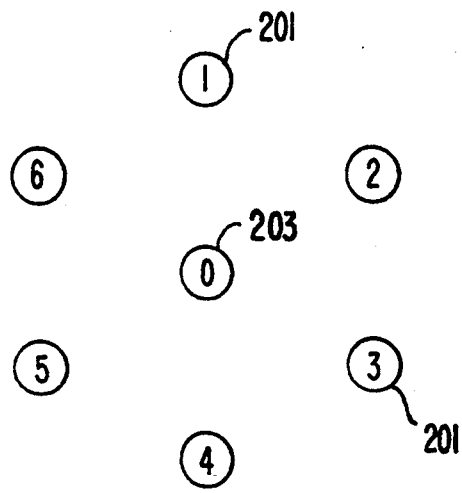
FIG. 5a is a top plan view of the seven-electrode configuration of FIG. 2b, as powered by a multi-phase supply.

FIG. 5a is a top plan view of the seven-electrode configuration of FIG. 2b, as powered by a multi-phase supply. The configuration comprises of a central electrode 203 or (0) uniformly surrounded by peripheral electrodes 201 or (1)–(6). Although the multi-phase RF power supply is not explicitly shown, it will be understood that the electrodes (0)–(6) are respectively connected to the $V_{10}$–$V_{60}$ voltage sources of the power supply 220 shown in FIG. 2b.

It can be seen from FIG. 5a that the central electrode (0) is adjacent to all six peripheral electrodes (1)–(6). On the other hand, a peripheral electrode such as the electrode (1) is adjacent to electrodes (0), (2) and (6). The rest of the electrodes (3), (4) and (5) are one electrode removed from the electrode (1).

By proper application of the multi-phase power supply, current flow is easily established between a peripheral electrode such as (1) and its adjacent electrodes (0), (2) and (6). It is also possible to have substantial current flow between a peripheral electrode such as (1) and the farther electrodes such as (3), (4) and (5). This is achieved by appropriate adjustment of the voltage amplitude and phase in each electrode in the array.

The relation between current flow and phases among the electrodes is best illustrated by focusing attention on a peripheral electrode such as (1) and two of its adjacent electrodes such as (0) and (2).

Figure 5B:
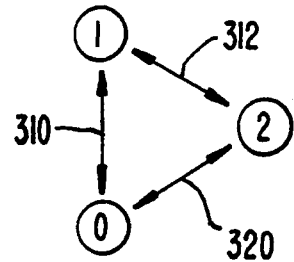

FIG. 5b illustrates the current distribution in a subset of adjacent electrodes (0), (1), (2) of the multi-electrode array shown in FIG. 5a. The electrodes (0), (1), (2) are respectively connected to the voltages $V_{00}$, $V_{10}$, $V_{20}$ shown in FIG. 2b. Therefore, the potential difference developed across electrodes (1) and (0) is $V_{10}$, and it causes a current to flow along a path 310 between the electrodes (1) and (0). Similarly, the potential difference developed across electrodes (2) and (0) is $V_{20}$, and it causes a current to flow along a path 320 between the electrodes (2) and (0). A third current path 312 between the electrodes (1) and (2) is best understood by reference also to FIG. 5c.

Figure 5C:
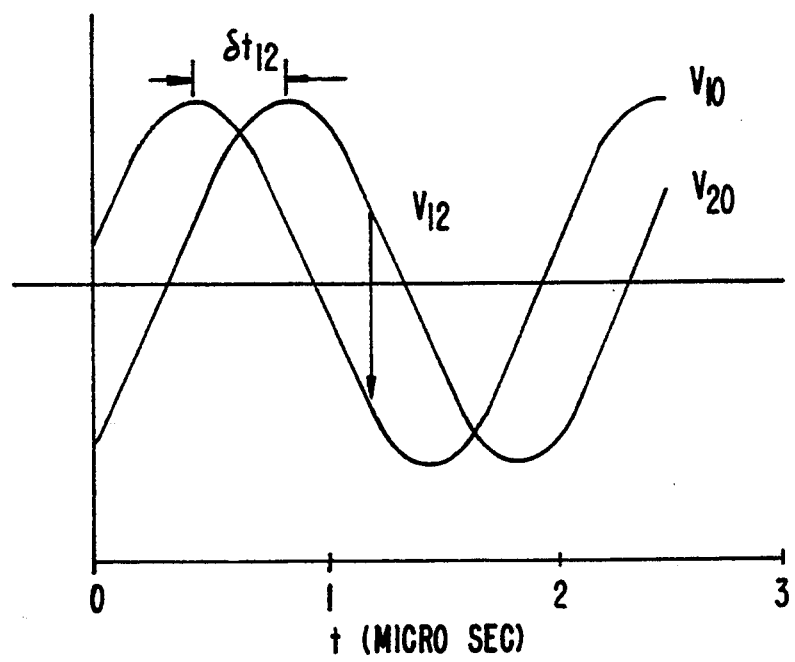
FIG. 5c illustrates the sinuosodial voltages $V_{10}$, $V_{20}$ as a function of time.

FIG. 5c illustrates the sinuosodial voltages $V_{10}$, $V_{20}$ as a function of time. When a phase difference $\delta\theta_{12}$ ($=2\pi f \delta t_{12}$) exists between the pair of voltages $V_{10}$, $V_{20}$, a potential difference $V_{12}$ is developed across the pair of adjacent electrodes (1) and (2). If $V_{10}$ and $V_{20}$ have the same amplitude, V, then, $$V_{12} = 2 V \sin(\delta\theta_{12}/2) \sin(2\pi ft)$$

where f is the frequency in hertz. This voltage in turn causes a current to flow along the path 312 between the electrodes (1) and (2).

Figure 6A:
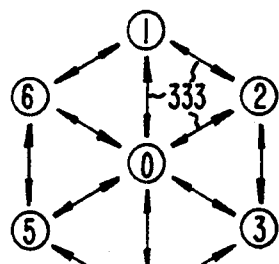
FIG. 6a illustrates the current distributions of a seven-electrode configuration as powered by a multi-phase supply.

FIG. 6a illustrates the current distributions of a seven-electrode configuration as powered by a multi-phase supply. The phase difference between each adjacent pair of electrodes results in a potential difference and allows the currents to flow therebetween. Thus a current path 333 is formed between each pair of adjacent electrodes. This provides a fairly complete coverage of the ablation zone spanned by the electrode array.

Conversely, if a single-phase RF power supply is used in conjunction with the seven-electrode configuration, current will flow only between a few pairs of electrodes.

Figure 6B:
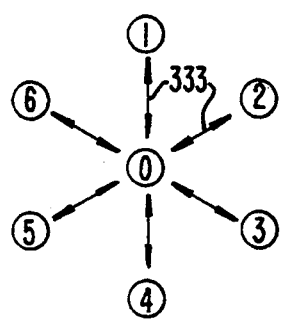
FIG. 6b illustrates the current distributions of a seven-electrode configuration as powered by a single-phase radio-frequency power supply.

FIG. 6b illustrates the current distributions of the seven-electrode configuration as powered by a single-phase radio-frequency power supply. With single-phase RF energy, a maximum number of current paths is achieved by connecting the central electrode (0) to the ground voltage $V_{00}$ of the single-phase power supply, and all the peripheral electrodes (1)-(6) to the voltages $V_{10}$-$V_{60}$ respectively. The resulting current paths 333 distribution forms a series of spokes, each joining the central electrode (0) to one of the peripheral electrodes (1)-(6). This leaves substantial areas in between where no current flows and therefore those areas are not subjected to adequate RF heating. A lesion formed in this manner will be very uneven and ineffective.

Figure 6C:
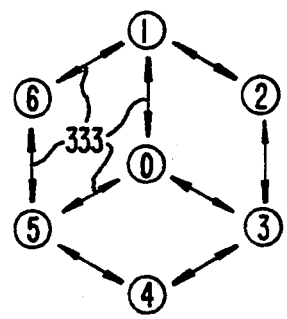
FIG. 6c also shows the current distributions for a variation of the seven-electrode configuration as powered by a single-phase radio-frequency power supply.

FIG. 6c also shows the current distributions for a variation of the seven-electrode configuration as powered by a single-phase radio-frequency power supply. In this case, the electrodes (0), (2), (4), (6) are connected to the ground voltage $V_{00}$ of the single-phase power supply, while the electrodes (1), (3), (5) are connected to the voltage $V_{10}$. The resulting current paths 333 distribution is illustrated in FIG. 6c. This also leaves substantial areas in between where no current flows and therefore those areas are not subjected to adequate RF heating. A lesion formed in this manner will also be very uneven and ineffective.

Apart from the benefit of a more uniform lesion, multi-phase RF ablation has been found to be much more efficient than single-phase ablation. Typically, a lesion is created in one quarter of the time (e.g. 5–20 sec) than that required for the single-phase case. This is advantageous since it reduces the risk of possible displacement of the catheter during an ablation operation.

The multi-phase RF ablations are typically conducted with delivered power in the range 10–40 W. The higher power setting being applied over a shorter duration such that the energy delivered each time is of the order of 100 joules.

It has been found that multi-phase RF ablation can not function satisfactorily unless certain restrictions on the dimensions of the electrodes are adhered to. One constraint is that the diameter of a smaller electrode in the array should be greater than approximately 0.7 times that of a larger electrode. Another constraint is that the total contact area of the electrodes with a tissue should be greater than approximately 0.2 times the area spanned by the array. Yet another constraint is that the average inter-electrode distance should be approximately less than 2.5 times the average diameter of the electrodes in the array.

TWO-PHASE RF ABLATION

In one preferred embodiment, a reasonably large lesion is created by multi-phase RF ablation with five electrodes. Furthermore, by judicious pairing of the electrodes, a two-phase RF supply is able to produce a fairly uniform lesion across the ablation zone spanned by the electrode array.

A preferred electrode array is a five-electrode orthogonal electrode catheter array (OECA) that has been mentioned earlier. The five-electrode OECA has been disclosed in U.S. Pat. No. 4,940,064. Relevant portions of said disclosure are incorporated herein by reference.

Figure 7A:
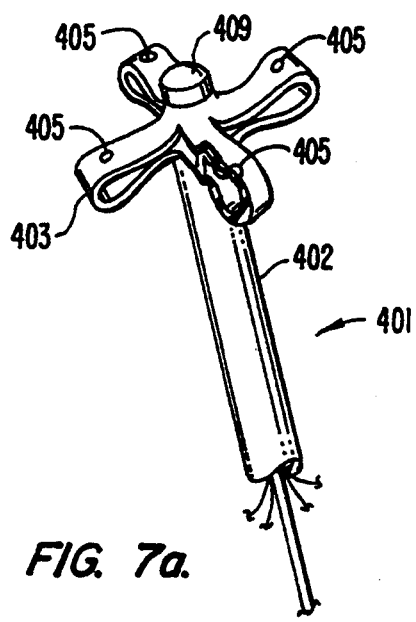
FIG. 7a illustrates the five-electrode orthogonal electrode catheter array (OECA) in its fanned-out state.

FIG. 7a illustrates the five-electrode OECA in its fanned-out state. The OECA comprises an eight-french five-pole electrode catheter 401. It has a central stylet 402 which when pulled from its distal end opens four side arms 403 in an orthogonal configuration. Each of the four arms 403 has a peripheral electrode 405 while the fifth electrode 409 is centrally located at the tip of the central stylet 402. All five electrodes are hemispherical. Each peripheral electrode 405 is 2 mm in diameter while the central electrode is 2.7 mm in diameter. The inter-electrode distance from the central electrode to each peripheral electrode is 0.5 cm, and the distance between peripheral electrodes is 0.7 cm. The surface area of the catheter tip in an open position is 0.8 cm².

Figure 7B:
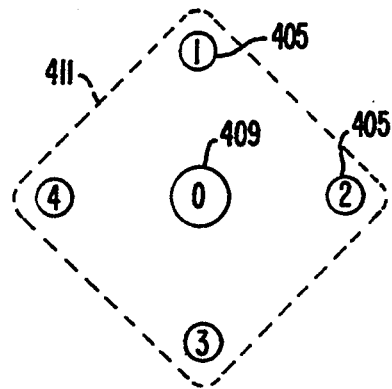
FIG. 7b shows the footprints of the five-electrode OECA.

FIG. 7b shows the footprints of the five-electrode OECA electrodes. The four peripheral electrodes 405 or (1)-(4) form a cross configuration. The fifth electrode 409 or (0) is located at the center of the cross. The orthogonal array of electrodes forms an RF ablation zone 411.

FIG. 8a illustrates the five-electrode OECA being used as a two-phase ablation apparatus according to a preferred embodiment. A 600-KHz RF, two-phase energy source produces voltages $V_{00}$, $V_{10}$, $V_{20}$, with $V_{00}$ being at ground potential and zero phase. The voltages $V_{10}$, $V_{20}$ are approximately the same amplitude but have a phase difference $\delta\theta_{12}$ in the range: 70°–110°. The central electrode 409 is connected to $V_{00}$. The peripheral electrodes 405 form two diagonal pairs. One pair is connected to $V_{10}$, and the other pair to $V_{20}$.

FIG. 8b illustrates the current distributions resulted from the two-phase configuration of FIG. 8a. Corresponding to that of FIG. 8a, the two pairs of diagonal electrodes are (1), (3) and (2), (4) and they are connected to voltages $V_{10}$, $V_{20}$ respectively. As explained earlier, this will allow RF currents to flow between electrodes whenever a sufficient potential difference exists. In this case, the RF current flow can be regarded as being of two sets for the purpose of discussion. One set is a cross configuration with current between the central electrode 409 and each of the peripheral electrodes 405. The other set results from potential differences between adjacent pairs of peripheral electrodes, with the current circumscribing all four peripheral electrodes 405. It can be seen that current paths 333 run across all adjacent pairs of electrode, substantially filling the ablation zone 411. Thus, a square-shaped lesion of approximately 1.2 cm$^2$ area is formed in the RF ablation zone 411.

Conversely, if a single-phase RF power supply is used in conjunction with the seven-electrode configuration, current will flow only between a few pairs of electrodes.

FIG. 9a illustrates the five-electrode OECA being connected in a single-phase configuration for the purpose of comparison with the two-phase configuration of FIG. 8a. In this case, a single-phase energy source only produces voltages $V_{00}$, $V_{10}$, with $V_{00}$ being at ground potential and zero phase. The central electrode 409 is connected to $V_{00}$. All four peripheral electrodes 405 are connected to $V_{10}$.

FIG. 9b illustrates the current distributions resulted from the single-phase configuration of FIG. 9a. Only the set of current flow associated with the cross configuration remains. This set of current paths is between the central electrode 409 or (0) and each of the peripheral electrodes 405 or (1)–(4). Since there is no potential difference between any of the peripheral electrodes (1)–(4), no current path is formed circumscribing the four peripheral electrodes. This arrangement is unsatisfactory, as it leaves the RF ablation zone 411 with substantial areas not covered.

Figure 10:
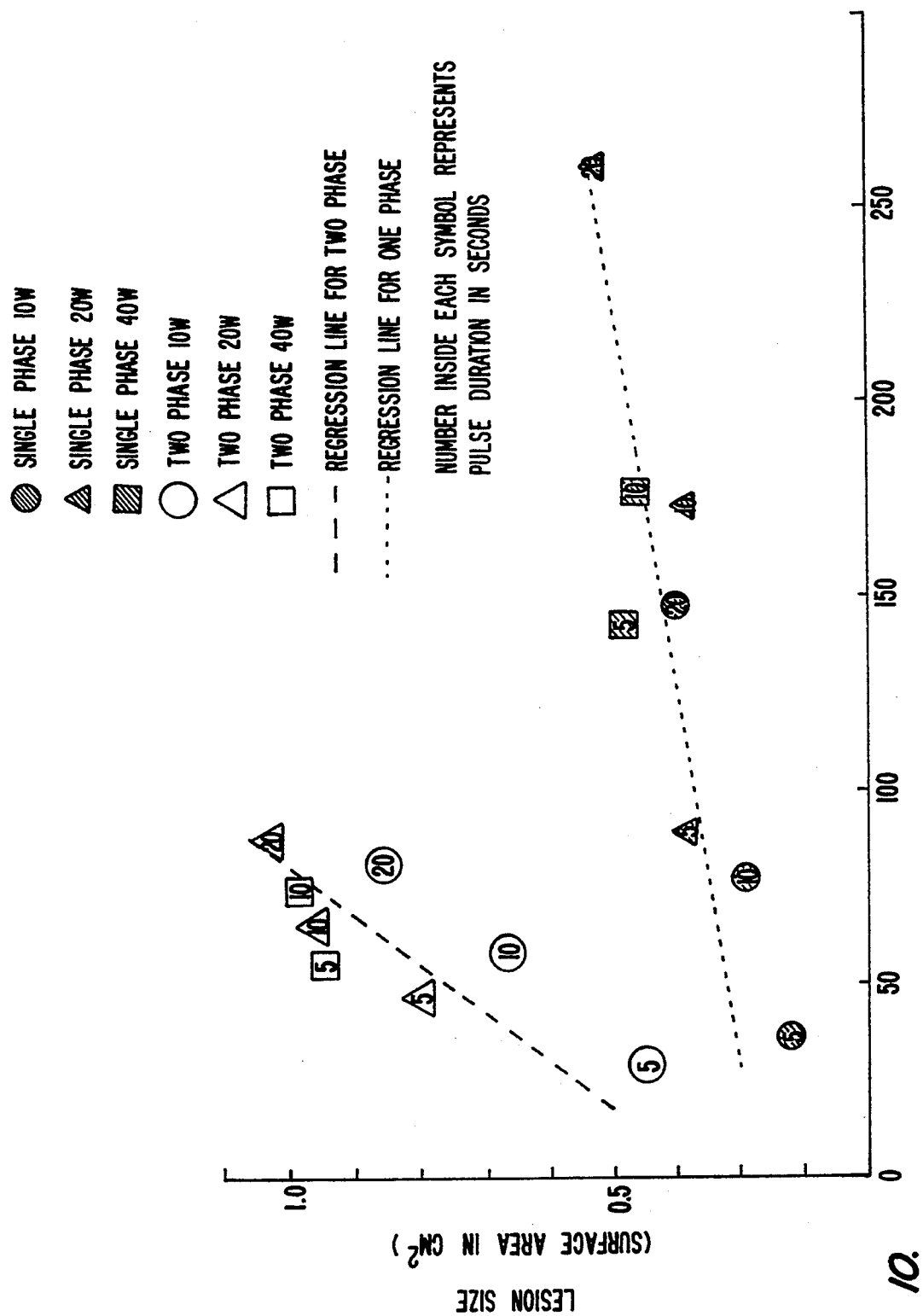
FIG. 10 shows a graph of lesions size versus ablation energy for various example operating parameters for both the two-phase and single-phase RF applications of the five-electrode OECA.

FIG. 10 shows a graph of lesions size versus ablation energy for various example operating parameters for both the two-phase and single-phase RF applications of the five-electrode OECA. Two-phase RF ablation produces a greater change in the size of lesion per unit additional energy used (0.0081 cm$^2$/J Vs. 0.00125 cm$^2$/J) than the single-phase case. The lesions produced by two-phase ablation are double in size and utilize half of the total energy compared to that produced by single-phase ablation. In two-phase ablation, in order to have greater control over the size of the lesions formed, it is preferable to have the power setting at 10 watts (0.0079 cm$^2$/J) rather than at 20 watts (0.0055 cm$^2$/J) or 40 watts (0.0022 cm$^2$/J). The largest lesions produced with the two-phase RF configuration (at 20 watts for 20 seconds) is found to be approximately 1.2 cm$^2$.

FIG. 11 illustrates the formation of a still larger lesion by successive adjacent ablations. For example, lesions of the order of 6 cm$^2$ is probably required for ablative treatment of ventricular tachycardia (VT). A larger lesion 451 of this size can be created by six adjacent square-shaped lesions 411. They can be formed by successive placements of the five-electrode OECA using two-phase RF energy. After each ablation, the electrode catheters is usually withdrawn to clean blood coagulum on the electrodes before the next attempt. The location of the next spot to be ablated is located by endocardiac mapping techniques such as ones described in a journal article by Desai et al, entitled, "Orthogonal Electrode Catheter Array for Mapping of Endocardiac Focal Site", published in *Pacing And Clinical Electrophysiology*, Volume 14, pp. 557–574, April 1991. Relevant portions of the Desai et al publication is incorporated herein by reference.

Temperature Regulated Multi-phase RF Ablation

The two-phase RF ablation scheme produces early impedance rise as seen by the power supply due to efficient necrosis of tissues and possibly early coagulum formation at the electrode tips. The formation of coagulum has the effect of restricting the current flow through the tissues and limiting the depth of lesion formation. It is possible to alleviate this problem by tightly regulating the ablation temperature.

Electrode tip temperature control has been implemented for conventional single-phase RF, standard electrode catheters ablation. This is disclosed in the journal article by Haines and Watson, "Tissue heating during radiofrequency catheter ablation: A thermodynamic model and observations in isolated profused and superfused canine right ventricular free wall" *PACE*, vol. 12, 1989, pp. 962–976. Relevant portions of the Haines and Watson article are incorporated herein by reference.

FIG. 12 shows a multi-phase RF ablation system having electrode tip temperature control, according to the present invention. An electrode catheter array 501 establishes electrical contact with a multi-phase power supply 511 by means of connections 521. One or more temperature monitors such as thermistors 531 are incorporated in the electrodes 541 of the electrode array to monitor temperatures during ablation. The RF power supply 511 incorporates a power control circuit 551 that controls the power output to the electrode catheter array 501 in response to the temperature monitors 531. The signals from the temperature monitors 531 is passed through lines 553 from the catheter to the power control circuit 551. Thus, the ablation temperature can be maintained at an optimum predetermined level, preferably about 80° C. This would prevent early coagulum formation and help to produce larger and deeper lesions with more uniformity.

While the embodiments of the various aspects of the present invention that have been described are the preferred implementation, those skilled in the art will understand that variation thereof may also be possible. The device and method described therein are applicable to ablation of biological tissues in general. Therefore, the invention is entitled to protection within the full scope of the appended claims.

It is claimed:

1. A radio-frequency ablation apparatus for biological tissues, comprising:

an electrode catheter having an array of electrodes; and means for supplying individual phased RF voltages to each of said plurality of electrodes, such that, over a predetermined period of time, substantial potential difference exists between substantially any two electrodes of said array of electrodes and to effect RF heating therebetween in order to achieve uniform ablation of biological tissues adjacent to said array of electrodes.

2. A radio-frequency ablation apparatus for biological tissues as in claim 1, wherein:
the diameter of a smaller electrode is greater than 0.7 times that of a larger electrode in the array.

3. A radio-frequency ablation apparatus for biological tissues as in claim 1, wherein:
an array coverage area is defined by the span of said array of electrodes, and an electrode contact area is defined by the contact area said electrode made with a biological tissue; and
the sum of all electrodes' contact areas is greater than 0.2 times that of the array coverage area.

4. A radio-frequency ablation apparatus for biological tissues as in claim 1, wherein:
the average distance between the electrodes in the array is less than 2.5 times the average diameter of the electrodes in the array.

5. A radio-frequency ablation apparatus for biological tissues as in claim 1, further comprising:
a temperature sensor in said array of electrodes for sensing temperature of ablation; and
means for regulating said individual phased RF voltages in response to said temperature sensing in order to maintain a predetermined temperature of ablation.

6. A radio-frequency ablation apparatus for biological tissues, comprising:
an electrode catheter having an array of electrodes;
a plurality of adjacent electrode pairs among said array of electrodes, each formed by an electrode and one of its immediate neighboring electrodes; and
means for supplying phased RF voltages to each of said plurality of adjacent electrode pairs, such that, over a predetermined period of time, substantial potential differences exist between each adjacent electrode pair to effect RF heating therebetween in order to achieve uniform ablation of biological tissues adjacent to said array of electrodes.

7. A radio-frequency ablation apparatus for biological tissues as in claim 6, wherein:
the diameter of a smaller electrode is greater than 0.7 times that of a larger electrode in the array.

8. A radio-frequency ablation apparatus for biological tissues as in claim 6, wherein:
an array coverage area is defined by the span of said array of electrodes, and an electrode contact area is defined by the contact area said electrode made with a biological tissue; and
the sum of all electrodes' contact areas is greater than 0.2 times that of the array coverage area.

9. A radio-frequency ablation apparatus for biological tissues as in claim 6, wherein:
the average distance between the electrodes in the array is less than 2.5 times the average diameter of the electrodes in the array.

10. A radio-frequency ablation apparatus for biological tissues as in claim 6, further comprising:
a temperature sensor in said array of electrodes for sensing temperature of ablation; and
means for regulating said individual phased RF voltages in response to said temperature sensing in order to maintain a predetermined temperature of ablation.

11. A radio-frequency ablation apparatus for biological tissues, comprising:
an electrode catheter having an array of five electrodes constituting first and second pairs of spaced-apart electrodes and an odd electrode, said first and second pairs of electrodes being disposed in substantially a cross configuration, and the odd electrode being disposed centrally at the cross configuration;
a radio-frequency energy source for providing two-phase voltages over a first pole, a second pole and a common pole;
means for connecting said first pole to said first pair of electrodes, and connecting said second pole to said second pair of electrodes, and connecting said common pole to said odd electrode; and
means for regulating said radio-frequency power source to provide said two-phase voltages with a predetermined frequency, voltage and phase difference such that, over a predetermined period of time, substantial potential differences exist between said odd central electrode and said first and second pairs of electrodes as well as between said first and second pairs of electrodes to effect RF heating therebetween in order to achieve uniform ablation of biological tissues adjacent said array of five electrodes.

12. A radio-frequency ablation apparatus for biological tissues as in claim 11, wherein:
the phase difference between said two-phase voltages is in the range of 70° to 110 degrees.

13. A radio-frequency ablation apparatus for biological tissues as in claim 11, wherein:
the diameter of a smaller electrode is greater than 0.7 times that of a larger electrode in the array.

14. A radio-frequency ablation apparatus for biological tissues as in claim 11, wherein:
an array coverage area is defined by the span of said array of five electrodes, and an electrode contact area is defined by the contact area said electrode made with a biological tissue; and
the sum of all electrodes' contact areas is greater than 0.2 times that of the array coverage area.

15. A radio-frequency ablation apparatus for biological tissues as in claim 11, wherein:
the average distance between the electrodes in the array is less than 2.5 times the average diameter of the electrodes in the array.

16. A radio-frequency ablation apparatus for biological tissues as in claim 11, further comprising:
a temperature sensor in said array of five electrodes for sensing temperature of ablation; and
means for regulating said individual phased RF voltages in response to said temperature sensing in order to maintain a predetermined temperature of ablation.

17. A method of ablating biological tissues, comprising the steps of:
providing an electrode catheter having a plurality of electrodes;
placing said electrode catheter near a region of biological tissues to be ablated;
deploying said plurality of electrodes into a two-dimensional or three-dimensional electrode array;

scanning the region of biological tissues to be ablated with said electrode array in connection with a mapping device;

locating with the mapping device one or more focal sites to be ablated according to the electrical response of said electrode array placed thereat; and supplying individual phased RF voltages to each of said plurality of electrodes, such that, over a predetermined period of time, substantial potential difference exists between substantially any two of said plurality of electrodes and to effect RF heating therebetween in order to achieve uniform ablation of biological tissues adjacent to the electrode array.

18. A method of ablating biological tissues as in claim 17, wherein:

the diameter of a smaller electrode is greater than 0.7 times that of a larger electrode in the array.

19. A method of ablating biological tissues as in claim 17, wherein:

an array coverage area is defined by the span of the deployed electrode array, and an electrode contact area is defined by the contact area said electrode made with a biological tissue; and the sum of all electrodes' contact areas is greater than 0.2 times that of the array coverage area.

20. A method of ablating biological tissues as in claim 17, wherein:

the average distance between the electrodes in the array is less than 2.5 times the average diameter of the electrodes in the array.

21. A method of ablating biological tissues as in claim 17, further comprising the steps of:

sensing the temperature during ablation by one or more temperature sensors among the electrode array; and regulating said individual phased RF voltages in response to said temperature sensing in order to maintain a predetermined temperature of ablation.

22. A method of ablating biological tissues as in claim 17, further comprising the steps of:

successively ablating adjacent areas in the biological tissues by the method thereof until a lesion of predetermined size is created.

* * * * *